United States Patent [19]
Patterson et al.

[11] Patent Number: 5,613,956
[45] Date of Patent: Mar. 25, 1997

[54] CATHETER INTRODUCER

[75] Inventors: Frank Patterson, Exeter, N.H.; John Zhang, Arlington, Mass.; George Purtell, Westford, Mass.; James Culhane, Westborough, Mass.

[73] Assignee: C. R. Bard, Inc., Murray Hill, N.J.

[21] Appl. No.: 241,627

[22] Filed: May 12, 1994

Related U.S. Application Data

[63] Continuation-in-part of Ser. No. 58,594, May 7, 1993.

[51] Int. Cl.$^6$ ........................................... A61M 25/00
[52] U.S. Cl. ..................... 604/256; 604/247; 604/167
[58] Field of Search .......................... 604/246, 247, 604/249, 167, 264, 280, 256; 251/149.1

[56] References Cited

U.S. PATENT DOCUMENTS

| | | |
|---|---|---|
| 4,610,674 | 9/1986 | Suzuki et al. . |
| 4,649,904 | 3/1987 | Krauter et al. . |
| 4,798,594 | 1/1989 | Hillstead . |
| 4,857,062 | 8/1989 | Russell . |
| 4,885,507 | 12/1989 | Patton et al. . |
| 4,895,565 | 1/1990 | Hillstead . |
| 4,932,633 | 6/1990 | Johnson et al. . |
| 4,960,412 | 10/1990 | Fink . |
| 5,000,745 | 3/1991 | Guest et al. . |
| 5,009,391 | 4/1991 | Shegerwald . |
| 5,059,186 | 10/1991 | Yomamoto et al. . |
| 5,084,023 | 1/1992 | Lemieux . |
| 5,098,393 | 3/1992 | Amplatz et al. . |
| 5,104,389 | 4/1992 | Deem et al. . |
| 5,114,408 | 5/1992 | Fleischhaker et al. ............ 604/167 |
| 5,125,910 | 6/1992 | Freitas . |
| 5,167,637 | 12/1992 | Okada et al. . |
| 5,195,980 | 3/1993 | Catlin . |
| 5,211,634 | 5/1993 | Vallancourt . |
| 5,242,413 | 9/1993 | Heiliger . |
| 5,242,428 | 9/1993 | Palestront . |
| 5,254,097 | 10/1993 | Schock et al. . |
| 5,267,982 | 12/1993 | Sylvanowicz . |
| 5,273,545 | 12/1993 | Hunt . |
| 5,304,156 | 4/1994 | Sylvanowicz et al. ............ 604/256 |

FOREIGN PATENT DOCUMENTS

| | | |
|---|---|---|
| 0308815 | 3/1989 | European Pat. Off. . |
| 344907 | 12/1989 | European Pat. Off. . |
| 0442194A2 | 8/1991 | European Pat. Off. . |
| 0442194 | 8/1991 | European Pat. Off. ............ 604/167 |
| WO93/25252 | 12/1993 | WIPO . |

OTHER PUBLICATIONS

Durometr Chart–Polyuretrones: The Bridge Between Silicone rubber and Plastics.

*Primary Examiner*—Corrine M. Maglione
*Assistant Examiner*—Chalin Smith
*Attorney, Agent, or Firm*—Bookstein & Kudirka, P.C.

[57] ABSTRACT

An improved self-sealing gasket provides hemostasis while reducing the force required to move a catheter or guidewire positioned within the gasket. Slits formed on one surface of the gasket intersect with a central aperture formed on the opposite face of the gasket. An annular ring formed on the gasket assists in retaining the gasket within a catheter introducer. An annular shelf may be provided distally of the gasket to prevent dislodgement of the gasket if an instrument is inserted into the introducer off axially.

20 Claims, 5 Drawing Sheets

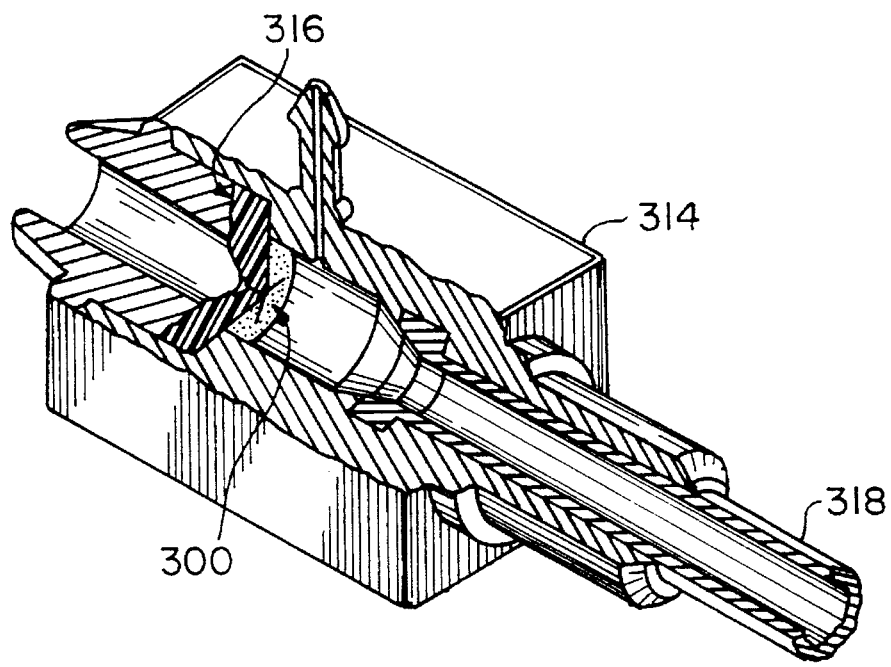
Fig.4
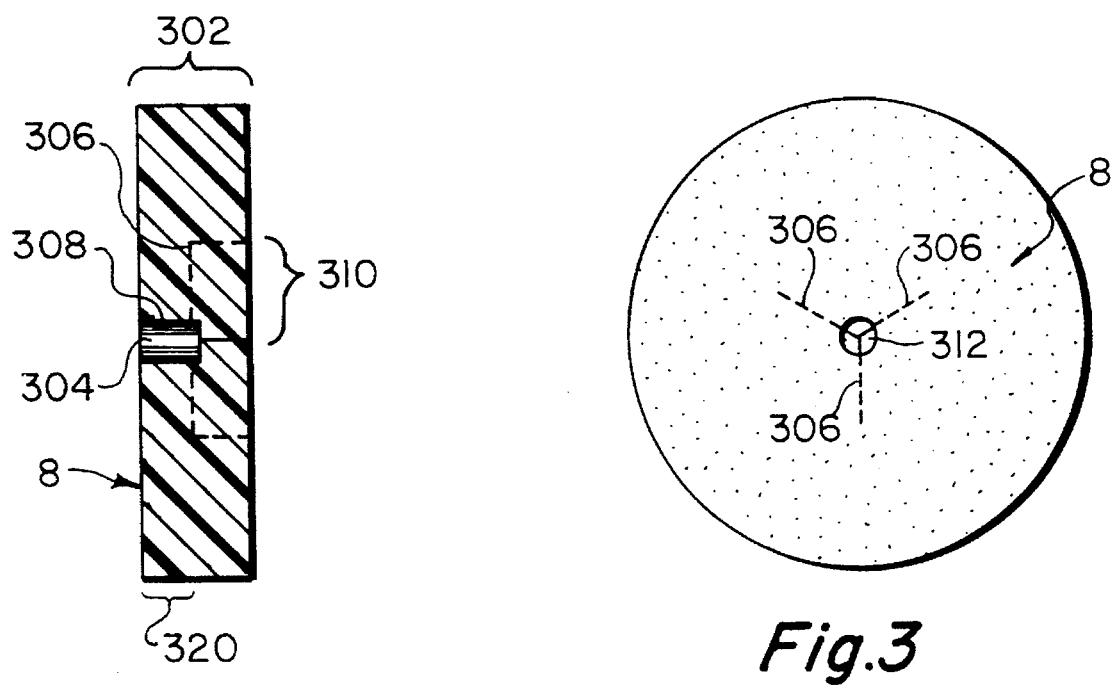
Fig.2
Fig.3

CATHETER INTRODUCER

RELATED APPLICATIONS

This application is a continuation-in-part of U.S. patent application Ser. No. 08/058,594, filed May 7, 1993.

FIELD OF THE INVENTION

This invention relates to improvements in vascular catheter introducers used in the introduction, manipulation and removal of catheters, guidewires and other instruments from a patient's vascular system in angiographic, angioplasty and other vascular procedures. The invention relates to introducers having an improved self-sealing gasket to maintain hemostasis while reducing the resistance to movement of a catheter, guidewire or other instrument as it is passed through and manipulated through the introducer.

Background of the Invention

A catheter introducer is a device that is placed, usually percutaneously, into a patient's body, such as into the vascular system for angiographic, angioplasty or other medical procedures. A catheter introducer typically includes a tubular shaft that is insertable into the patient's vascular system or other body region and a housing attached to the proximal end (the end disposed outside of the patient) of the tubular shaft. The housing contains and supports one or more self-sealing hemostasis gaskets that close to prevent blood leakage when no instrument is present in the introducer and to maintain a seal against and about such instrument to prevent blood loss while the instrument is in place through the introducer.

In addition to providing a hemostasis seal, both when an instrument is or is not present in the introducer, it is important that the gasket presents minimal drag and resistance to movement to the catheter, guidewire or other instrument in order to facilitate manipulation of the instrument in the patient. The tactile response that the physician senses at the proximal end of the instrument is important to the physician in order that he can feel obstructions or tortuous vascular anatomy as the instrument is advanced through that anatomy. Typically, hemostasis gaskets for catheter introducers have involved a compromise between maintaining an effective seal under all conditions of use and the resistance to movement that the gasket imposes on a medical instrument.

Prior art devices have addressed the desirability of maintaining a seal without unduly impairing the ease of movement of the catheter through the gasket. Introducers may be made with self-sealing gaskets adapted to receive and effect a seal only with instruments having a limited range of diameters. That typically has been less than satisfactory because it is common to require the use of a number of guidewires and catheters that must be inserted through the introducer having diameter ranges of between about 0.035 inch to 0.118 inch or more. The self-sealing hemostasis gaskets disclosed in U.S. Pat. Nos. 4,000,739 (Stevens) and 4,424,833 (Spector) are representative of prior art gaskets designed to receive a specific size of instrument and adapted to accommodate a relatively limited range of instrument diameters.

U.S. Pat. No. 5,304,156 (Sylvanowicz) assigned to the assignee of the present invention discloses an improved catheter and guidewire introducer that has a self-sealing gasket adapted to effect a seal both in the presence and in the absence of a guidewire or catheter and where the range of diameters of guidewires and catheters that can be accepted is substantially greater than the art that preceded it, including the devices described in the Stevens and Specter patents. Moreover, the device described in the Sylvanowicz patent effected a seal over a wide range of devices while not significantly impairing the feel of the catheter as it is manipulated through the introducer. Notwithstanding the improvements achieved with the device described in the Sylvanowicz patent, it would be desirable to further improve the device by further reducing the drag imposed on the catheter or the guidewire by the gasket while still maintaining an effective hemostasis seal. Additionally, it would be desirable to enhance the manner in which the gasket is anchored in the housing, particularly so that when relatively large diameter catheters are inserted through the gasket, the gasket is retained securely in place in the housing and will resist any tendency for the relatively large diameter catheter to dislodge the gasket. It also is appreciated that instruments presented to the gasket off angle may dislodge the gasket from the housing, which could lead to a loss of hemostasis. An introducer which prevents detachment of the gasket in such situations would be desirable. It is among the objects of the present invention to provide such an improved introducer and gasket.

SUMMARY OF THE INVENTION

In one aspect of the invention, the gasket has a geometry similar to that described in Sylvanowicz U.S. Pat. No. 5,304,156 and application Ser. No. 08/058,594 but modified to provide still further improvements by reducing the frictional drag between the catheter and the gasket in combination with optimized material characteristics for the gasket. In particular, the gasket is made substantially thinner than that described in the Sylvanowicz patent and even thinner than that described in application Ser. No. 08/058,594. In another aspect of the invention, the gasket is modified to include improved anchoring means by which the gasket is more firmly secured in the housing. That is particularly desirable with the thinned configuration gasket which, because of its thin construction, might otherwise display an increased tendency to be dislodged when a large diameter catheter is inserted through the gasket.

It is among the objects of the present invention to provide a gasket that can be utilized in a catheter introducer to provide increased ease of movement while maintaining hemostasis of a wide range of diameters of catheters and guidewires that can be passed through the gasket.

Another object of the invention is to provide a catheter introducer having a gasket that is thinner and provides improved material characteristics over prior catheter introducer gaskets to allow improved tactile response for the physician while maintaining hemostasis over extended periods of time.

Yet another object of the invention is to provide an improved catheter introducer having a one-piece hemostasis gasket and an improved means for anchoring the gasket to resist its being dislodged when a large diameter catheter is inserted.

Still another object of the invention is to provide a annular retaining shelf within the housing which prevents dislodgement of the gasket during insertion of medical instruments through the gasket while allowing for limited deflection of the gasket.

A still further object of the invention is to provide an introducer which attempts to correct off angle introduction of an instrument and, additionally, which reduces the incidence of dislodgement of the gasket when the instrument is being inserted off-axially.

DESCRIPTION OF THE DRAWINGS

The foregoing and other objects and advantages of the invention will be appreciated more fully from the following further description thereof, with reference to the accompanying drawings wherein:

FIG. 2 is a cross-sectional view of the gasket of the present invention.

FIG. 3 is another view of the gasket of the present invention illustrating the slits as viewed from the surface of the gasket containing the central aperture.

FIG. 4 is an illustration of the gasket of the present invention mounted in the housing of the catheter introducer section to illustrate the internal structure of the housing.

DESCRIPTION OF THE ILLUSTRATIVE EMBODIMENTS

Figure 1:
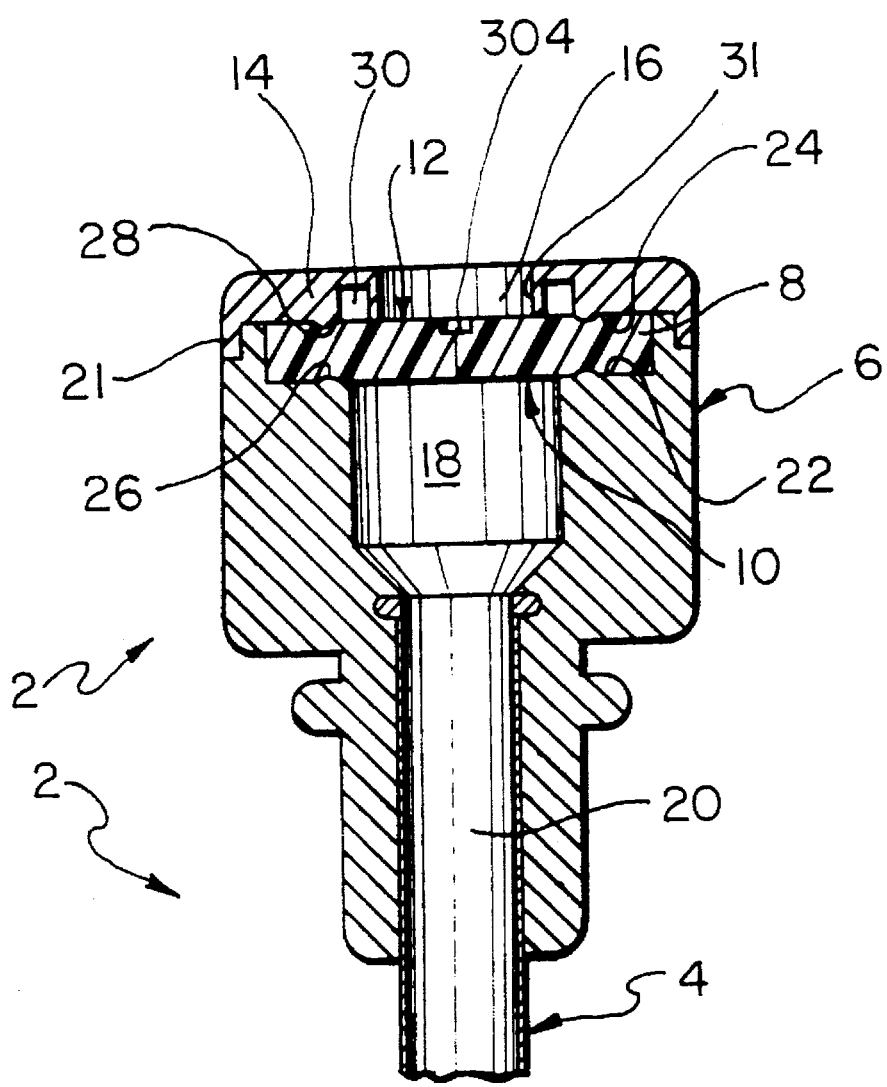
FIG. 1 is a schematic illustration of a housing of a catheter introducer sectioned to illustrate the internal structure of the housing and the gasket contained therein.

FIG. 1 illustrates, in section, the proximal portion of a catheter introducer 2 including a proximal housing 6 and a small portion of a tubular sheath 4 that is attached to and extends distally from the housing 6. The tubular sheath is intended to be inserted into a patient's blood vessel, typically in a percutaneous procedure.

The housing contains a self-sealing hemostasis gasket 8 having a geometry illustrated in FIGS. 2 and 3 and in the aforementioned U.S. Pat. No. 5,304,156 and application Ser. No. 08/058,594, the disclosures of which are incorporated herein by reference in their entireties.

The gasket 8 is disk shaped and is captured between the housing 6 and an end cap 14 secured to the proximal end of the housing 6. The end cap 14 is provided with an aperture 16 through which catheters and guidewires may be inserted through the gasket 8, the interior 18 of the housing and the lumen 20 of the shaft 4. The cap 14 may be provided with a circumferential lip 21 that mates with a shoulder on the proximal end of the housing 6. Other configurations for attachment of the cap to the housing may be provided. The end cap and housing may be joined by any of a variety of gluing or welding techniques known to those skilled in the art for securing such plastic components together. The housing and end cap each have annular surfaces 22, 24 that face each other, when assembled, and engage, respectively, the distal and proximal surfaces 10, 12 of the gasket 8. In order to further secure the gasket 8 between the housing and the end cap, each of the annular surfaces 22, 24 may be provided with circumferential ridges 26, 28, adapted to securely press into the surfaces 10, 12 of the gasket 8.

The cap may be provided with an annular reservoir 30 to retain a lubricant as described in application Ser. No. 08/058,594. The reservoir may take the form of an annular slot 30 formed in the distal face of the end cap. The surface of the end cap that defines the aperture 16 serves as a lip 31 to partly define the reservoir 30. The distal edge of the lip normally contacts the proximal surface 12 of the gasket to retain the lubricant but to permit it to be released when the gasket 8 is flexed upon insertion of a catheter. The functioning of the reservoir is described more fully in application Ser. No. 08/058,594.

FIGS. 2 and 3 illustrate the gasket which is geometrically similar to that disclosed in U.S. Pat. No. 5,304,156 and application Ser. No. 08/058,594. The gasket 8 differs from the gaskets described in the patent and application in several respects. The gasket 8 is thinner, of the order of 0.050 inch thickness. Additionally, central aperture 304 in the proximal face of the gasket, although the same diameter as in the above-referenced patent and application (0.029 inch) is not as deep, being of the order of 0.020 inch because the gasket 8 is substantially thinner than that disclosed in the patent.

As noted above, a preferred total thickness of the gasket is 0.05 inch. The slits 306 have a depth of 0.036 inch. The central aperture has a depth of 0.020 inch, with the slits extending into the radial walls 308 of the central aperture a distance of 0.006 inch. By extending the slits through and into the walls 308 of the central aperture, the gasket is weakened about the central aperture so that it can yield to a relatively large diameter catheter that is forced through the central aperture, even when the catheter diameter is much greater than that of the central aperture. Significantly, with the present invention, a relatively large catheter can be advanced through the gasket but with even less resistance and improved feel over the gasket configurations described in U.S. Pat. No. 5,304,156 and application Ser. No. 08/058,594.

Providing only partial slitting of the central aperture has the additional advantage that guidewires, typically 0.035 to 0.038 inch in diameter, will also be sealed by the 0.029 inch diameter central aperture. While the depth of the slits into one face of the gasket and the depth of the central aperture into the opposite face of the gasket may be varied, it is important that the slits extend a distance into the radial walls 308 which are formed by the central aperture. In the preferred embodiment, the central aperture has a depth of 0.020 inch while the preferred slit depth is 0.036 inch.

In the preferred embodiment, the slits 306 preferably have a radial length 310 of 0.030 inches, giving a total slit diameter of 0.060 inch. This radial diameter of the slits differs from the diameter given in U.S. Pat. No. 5,304,156 which has a longer radial diameter of 0.075 inch radial length and, thus, a total slit diameter of 0.150 inch. In the present invention, the slits can be made of a smaller radial diameter because of the relatively thinner thickness of the gasket. Were the slits to be made of a radial length the same or similar to that of that described in U.S. Pat. No. 5,304,156, the gasket might tend to leak both in the presence of a guidewire or catheter in the gasket as well as without such an instrument through the gasket, due to blood pressure. Thus, the thinner gasket of the present invention provides the hemostasis ability of a thicker gasket but as well provides a relative ease of movement of catheters through the gasket.

An additional factor affecting both hemostasis and the "feel" and ease of movement of a guidewire or catheter through a gasket is the particular material which is used for the construction of the gasket. A stiffer material, for example, while perhaps providing good hemostasis, may impede the ease of movement of instruments inserted through the gasket. We have found that in the gasket of the present invention that certain ranges of hardness of materials of the gasket, preferably an elastomeric silicone, perform better than others. The maximum functional range for the hemostasis gasket of the present invention is a hardness of a durometer of 15 to 60 Shore A Durometer. A preferred range of hardness is 32–45 Shore A Durometer with a more preferable range of approximately 37±5 Shore A Durometer with the material in each of the cases being preferably made of an elastomer material, such as silicone and in the illustrative dimensions described herein. While the preferred thickness of the gasket has been given as 0.050 inches, it is understood that the ability of the present gasket to seal as well as to provide efficient "feel", the gasket may be made in a range from 0.040 inches to 0.060 inches. The overall hemostasis as well as ease of movement and "feel" is affected in the gasket of the present invention by the relative sizes of the depth of the central aperture, the depth of the slits, the radial length of the slits and the hardness and type of material used to form the gasket.

Although the FIGS. 2 and 3 show 3 slits, it should be understood that a greater or lesser number may be utilized, as is known to those skilled in the art in order to achieve the particular desired characteristics of the gasket to best achieve the desired goals of maintenance of hemostasis as well as ease of movement of catheters, guidewires and other instruments passed through the gasket.

The gasket 8, being relatively thin, lessens the amount of force required for catheter movement compared with a similar, but thicker, gasket while maintaining hemostasis. It is somewhat common in angiography and angioplasty procedures for there to be an interval between procedures after the catheter introducer has been placed in the patient's vascular system. For example, the introducer may be placed in a patient's system to perform angiographic testing to locate any obstruction in the patient's arteries. If such obstructions have been found, and an angioplasty procedure scheduled the next day, it is inconvenient to remove the catheter introducer and reinsert another introducer the following day. Instead, the introducer is left in place. To prevent abrading of the surrounding vessel by the tip of the introducer and to avoid kinking of the thin-walled sheath if the patient's body shifts or moves, an obturator is placed in the catheter. In a catheter introducer having a gasket with a thickness less than 0.050 inch, the extended use of the obturator may permanently deform the gasket, due to its thinness. The gasket will then be unable to maintain hemostasis during the subsequent angioplasty procedure. With a silicone elastomer gasket as described, approximately 0.050 inch thick, the ability to maintain hemostasis is retained despite the extended use of an obturator.

FIG. 3 shows another view of the gasket 8 of FIG. 1 as seen from the surface of the gasket in which the central aperture is formed. As can be seen in FIG. 3, the slits 306 are only through slits in the region 312 bounded by and defined by the central aperture. That is, while slits are cut through a predetermined depth into the surface of the gasket opposite that of the central aperture, the regions between the slits outside the periphery of the aperture are not "freely moving" due to the one-piece construction of the gasket. The region 312 in which the central aperture and the flaps between the slits overlap is freely movable. While the entire radial length of the slits does not freely move, the depth of the slits cut into the surface of the gasket weakens that surface allowing, in addition to the overlapping of the central aperture and the slits, the gasket to give way when a large diameter catheter is inserted through the gasket while maintaining the ability to seal around small diameter guidewires as well as due to the presence of the small diameter central aperture.

FIG. 4 illustrates a housing 314 into which the gasket 8 of the present invention is inserted. The gasket 8 is fitted into a a circular recess 316 within the housing 314. Tube 318 may be elongated and is designed to be inserted into a patient's vascular system.

Figure 5:
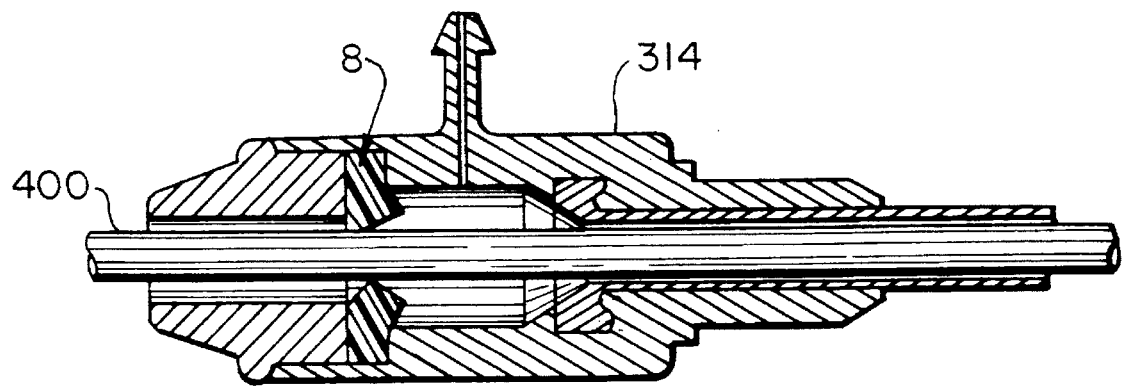
FIG. 5 illustrates the operation of the gasket of the present invention with a large diameter instrument inserted therethrough.
Figure 6:
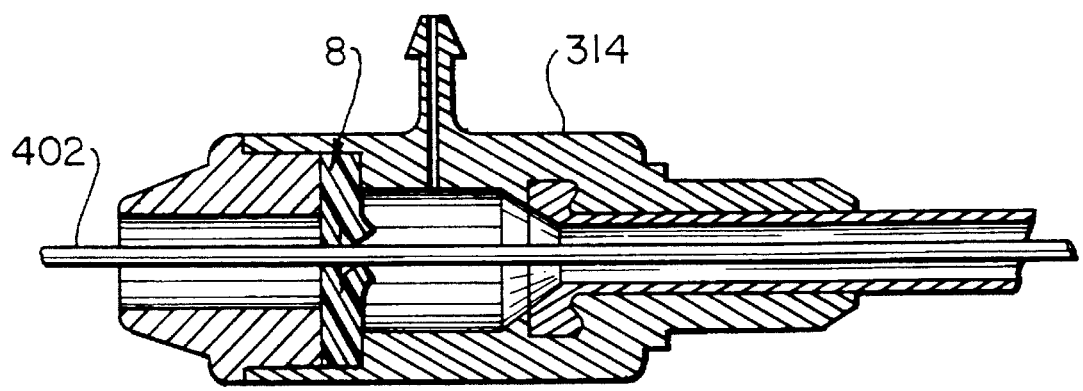
FIG. 6 illustrates the operation of the gasket of the present invention with a small diameter guidewire passed therethrough.

FIGS. 5 and 6 illustrate the operation of the gasket of the present invention with instruments of varying diameters passed therethrough. FIG. 5 illustrates the position of the gasket with a large diameter catheter or other instrument 400 passed through gasket 8. As can be seen in FIG. 5, the catheter is of a diameter much greater than the diameter of the central aperture 304 of FIG. 2. For example, the diameter of the aperture has been given as 0.029 inch, while a 8 French catheter which may be typically used with the gasket of the present invention, has a diameter of approximately 0.105 inch. The central aperture, upon insertion of the catheter, stretches and opens, assisted by the weakening of the radial walls provided by the overlapping slits and the slitting of the inwardly facing surface to allow the passage of a catheter therethrough. The catheter is sealed by the gasket 8 to maintain hemostasis. When the catheter is removed, the gasket returns to the position as shown in FIGS. 2 and 3.

FIG. 6 illustrates the operation of the present gasket with a guide wire or small catheter 402 passed therethrough. Because the guidewire is slightly, but not greatly, larger in diameter than the central aperture 304 shown in FIG. 2, the central aperture 304 stretches but is not deflected significantly, and the slitted portion of the gasket 8 will move out of the tube to allow the passage of the guidewire. When the guidewire is removed, the flaps formed by the slits return to their normal position shown in FIGS. 2 and 3.

Figure 7:
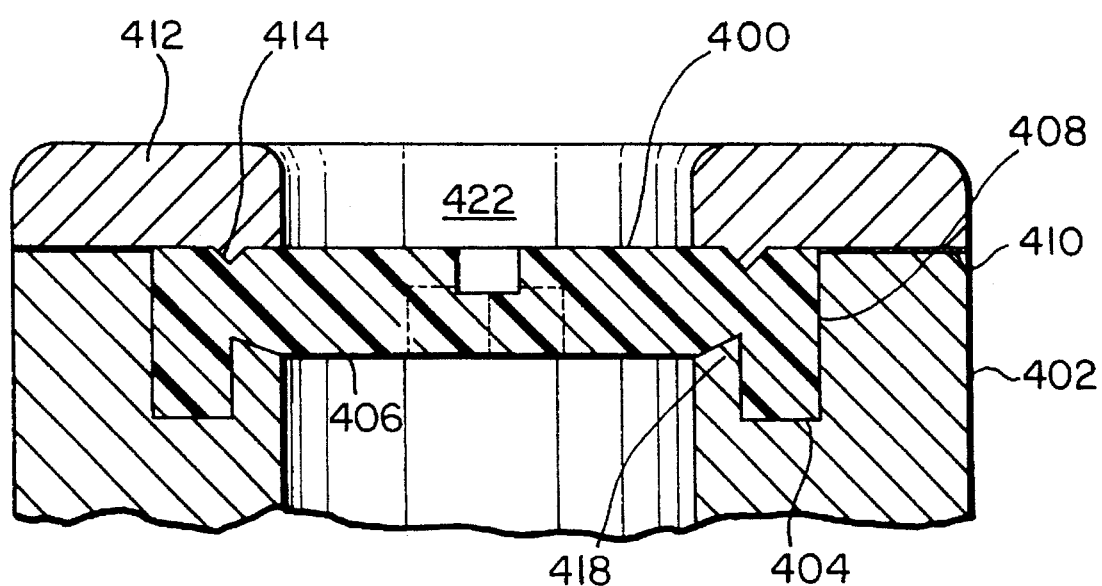
FIG. 7 illustrates another embodiment of the present invention with a retaining ring affixed to the gasket of FIGS. 2 and 3.

FIG. 7 illustrates another embodiment of the gasket of the present invention. Gasket 400 is shown installed within a housing 402 of a catheter introducer such as is shown in FIGS. 1 or 4 of the present invention. Gasket 400 is identical or substantially similar to the gasket 8 illustrated in FIGS. 2 and 3 except that an annular distally extending ring 404 is formed about the periphery of the face 406 of the gasket 400. The annular ring 404, which preferably is formed of the same material and in one-piece with the gasket 400 is received in an annular recess 408 formed in the end wall 410 of the housing 402. An end cap 412 is then assembled, by glue, welding or other well-known means, onto the end wall 410 to seal the housing 402 as well as to retain the gasket 400 on the side of the gasket containing the central aperture. Circular ribs 414, 418 are formed respectively in the end cap and in the housing 402 to press into the relatively resilient material of the gasket 400 to help with its retention within the housing. When a large catheter is passed through the end cap opening 422 into and through the gasket, due to the large size of the catheter, there is an increased risk that the gasket may become dislodged from its retaining structure.

By extending the gasket by means of the annular ring 404 and capturing the annular ring within an annular recess 408 as well as by fixing the periphery of the outside surface of the gasket by means of the end cap, the fixation of the gasket within the housing 402 is assured and dislodgement of the gasket is prevented. In addition to providing an annular ring on the inside surface 406 of the gasket, it is possible to additionally affix a similar ring on the outside surface (the surface containing the central aperture) and providing a complementary annular recess in the end cap 412 to provide even better retention of the gasket 400 within the housing 402. Alternatively, the annular ring 404 may be formed only on the outer surface of the gasket which mates with an annular recess in end cap 412, to retain the gasket.

Figure 8:
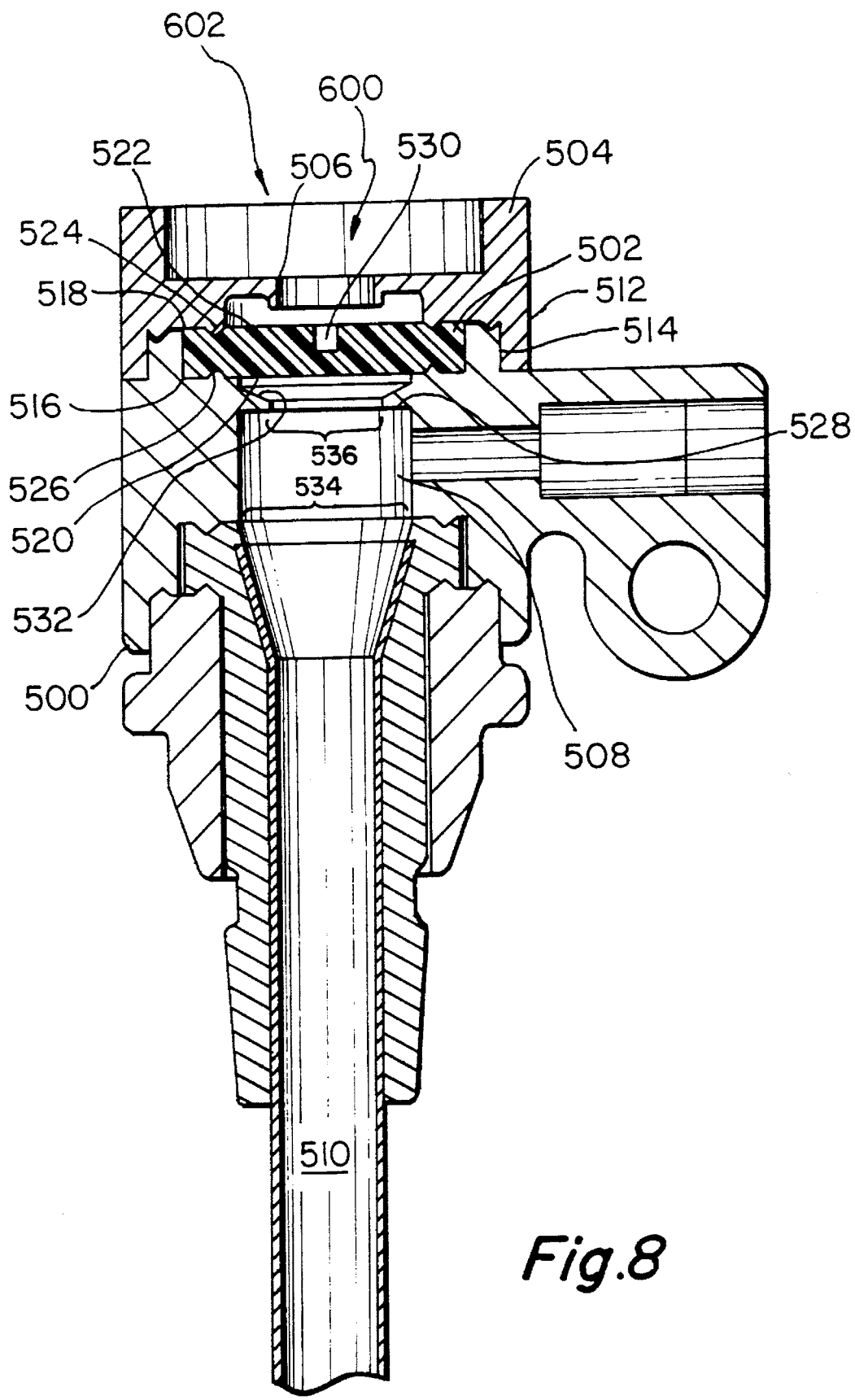
FIG. 8 illustrates yet another embodiment of the present invention in which a annular retaining shelf is formed within a catheter introducer housing.

FIG. 8 illustrates a modified version of the catheter introducer housing of FIG. 1 which includes an annular retaining shelf to prevent dislodgement of the gasket in the event that the physician attempts to push a medical instrument, such as an obturator, through the gasket at a non-axial angle (an insertion angle other than along the longitudinal axis of the housing 6 and lumen 20 of FIG. 1). Such action tends to dislodge the gasket from the grip of the circumferential ridges 26 and 28 shown in the housing of FIG. 1. FIG. 8 illustrates a proximal housing 500 which retains a gasket 502, which may be of the type illustrated in FIGS. 2 and 3. An end cap 504 is secured to the proximal end of the housing 500. Catheters, guidewires, obturators and other medical instruments may be inserted through the aperture 506, the gasket 502, the interior 508 of the proximal housing and into the lumen 510 located distally of the proximal housing 500.

As shown in FIG. 8, the cap 504 may be provided with a lip 512 which overlies and mates with a shoulder 514 formed at the proximal end of the housing 500. As described with respect to the housing of FIG. 1, various configurations for attachment of the cap to the housing may be provided. The housing and the cap each have annular surfaces 516 and 518 that face one another when assembled and engage respectively the distal and proximal surfaces 520 and 522 of the gasket 502. In order to further secure the gasket 502 between the housing and the end cap, each of the annular surfaces 516 and 518 may be provided with circumferential ridges 524 and 526 which press into the surfaces 520 and 522. In addition, the housing includes a annular protrusion or shelf 528 which extends inwardly from the annular surface 516. The annular shelf 528 projects into the interior 508 to reduce the diameter of the hole to less than the diameter of the interior space 508. The annular shelf 528 is preferably inclined at 532 in a distally facing angular direction on the side of the shelf which faces the surface 520 of the gasket.

The circumferential ridges 524 and 526 generally are sufficient to retain the gasket during axial insertion of guidewires, catheters and other medical instruments through the housing 500. However, if these instruments or a larger instrument such as a dilator is pushed through the aperture 506 and against the gasket at an angle rather than along the axis of the introducer (proper angle of insertion shown as arrow 600 and off-axial insertion shown as arrow 602), the tip of the dilator may not come into contact with the central aperture 530 of the gasket but rather with another portion of the surface 522. In that event, the tip of the dilator will not be pushing against the central aperture 530, which is designed to open to receive the dilator, but rather a surface which has no opening(s). The result is that the gasket may be dislodged from the circumferential ridges 524 and 526 retaining the gasket. Dislodgement of the gasket will cause a loss of hemostasis and potential dangers to the patient and physician alike due to blood loss. The annular shelf 528 solves the problem of gasket dislodgement by providing an abutting surface for the surface 520 of the gasket when the gasket is deformed by the force of a dilator or other instrument pressing on the outwardly facing surface 522 of the gasket. The annular shelf will not only reduce the possibility of the gasket becoming dislodged from the housing, but also tends to force the physician to center the tip of the dilator as the physician meets resistance in attempting to insert the dilator at an angle other than axially. In addition, even in an axial insertion of a dilator or other instrument, the annular shelf assists in limiting the amount of deflection of the gasket by abutment of the inwardly facing surface 520 of the gasket against the inclined surface of the shelf.

The annular shelf is preferably constructed with the inclined surface 532 to allow for some distal expansion or deflection of material forming the gasket, but having an outside limit for movement and deflection of the gasket well below the point of dislodgement. It has been found, for a housing having an interior diameter 534 of 0.200 inch, that an annular shelf preferably has an opening diameter 536 which may range from 0.140 inch to 0.175 inch. The minimum for opening diameter 536 is limited to the outside diameter of the largest catheter or other medical instrument which is to be inserted through the gasket. It has been found that even an annular shelf which reduces the inner bore diameter only by 0.010 inch to 0.015 inch is effective in retaining the gasket within the housing in the event of an attempted non-axial insertion of a medical instrument.

It should be understood that the foregoing description of the invention is intended merely to be illustrative thereof and that other modifications and embodiments may be apparent to those skilled in the art without departing from its spirit.

Having thus described the invention, what we desire to claim and secure by Letters Patent is:

1. A gasket for use in a catheter introducer having a housing that contains the gasket, the gasket comprising:

a self-sealing, one piece gasket having an inwardly facing surface, an outwardly facing surface, and a central aperture formed in its outwardly facing surface, the aperture extending a predetermined depth into the gasket and being defined in part by a circumferential wall;

a plurality of slits formed in the inwardly facing surface of the gasket and extending radially from a central region, the slits having a depth such that they intersect the circumferential wall, the central region of the slits overlapping the central aperture and defining a plurality of flaps normally closing the aperture;

the central aperture and the slits being dimensioned to enable the gasket to form a seal about a range of diameters of devices that includes guidewires and catheters; and an annular ring extending from and beyond the inner facing surface of the gasket, the ring being engageable by the housing to secure the gasket in the introducer.

2. A gasket for use in a catheter introducer having a housing that contains the gasket, the gasket comprising:

a self-sealing, one piece gasket having an inwardly facing surface, an outwardly facing surface, a central aperture in its outwardly facing surface, the aperture extending a predetermined depth into the gasket and being defined in part by a circumferential wall;

a plurality of slits formed in the inwardly facing surface of the gasket and extending radially from a central region, the slits having a depth such that they intersect the circumferential wall, the central region of the slits overlapping the central aperture and defining a plurality of flaps normally closing the aperture; and an annular ring extending from at least one of the inwardly facing surface or the outwardly facing surface of the gasket, the ring being adapted to be engaged by the housing to secure tho gasket in the housing.

3. The gasket as defined in claim 2 wherein the annular ring extends inwardly beyond the inwardly facing surface of the gasket.

4. The gasket as defined in claim 2 wherein the annular ring extends outwardly beyond the outwardly facing surface of the gasket.

5. The gasket as defined in claim 2 wherein the annular ring extends both outwardly and inwardly, respectively, from the outwardly facing surface and the inwardly facing surface.

6. A gasket for use in a catheter introducer having a housing that contains the gasket, the gasket comprising:

a self-sealing one piece gasket having an inwardly facing surface and an outwardly facing surface; and an annular ring extending from at least one of the inwardly facing surface or the outwardly facing surface of the gasket, the ring being adapted to be engaged by the housing to secure the gasket in the housing.

7. The gasket as defined in claim 6 wherein the annular ring extends from and beyond the inwardly facing surface of the gasket.

8. The gasket as defined in claim 6 wherein the annular ring extends from and beyond the outwardly facing surface of the gasket.

9. The gasket as defined in claim 6 wherein the annular ring extends both outwardly; and inwardly, respectively from the outwardly facing surface and the inwardly facing surface.

10. The gasket defined in claim 6 wherein the gasket includes a central aperture in its outwardly facing surface, the aperture extending a predetermined depth into the gasket and being defined in part by a circumferential wall.

11. The gasket defined in claim 10 further comprising:

the gasket having a central aperture formed in its outwardly facing surface, the aperture extending a predetermined depth into the gasket and being defined in part by a circumferential wall;

a plurality of slits formed in the inwardly facing surface of the gasket and extending radially from a central region, the slits having a depth such that they intersect the circumferential wall, the central region of the slits overlapping the central aperture and defining a plurality of flaps normally closing the aperture.

12. A catheter introducer comprising:

a housing having an inner bore, an outer bore proximal of and forming a juncture with the inner bore, a shoulder defined at the juncture of the inner bore and the outer bore, and an annular recess defined by the shoulder, the outer bore being larger in diameter than the inner bore;

a gasket having a diameter corresponding substantially to that of the outer bore, including an inwardly facing surface, an outwardly facing surface, and an annular ring extending from and beyond the inwardly facing surface of the gasket for cooperation with the annular recess in the shoulder;

a cap supported by the housing and contacting the outwardly facing surface of the gasket to secure the gasket in the housing.

13. The catheter introducer of claim 12 further including a reservoir for containing lubricating fluid being formed by a space between the cap and the outwardly facing surface of the gasket to lubricate medical instruments inserted through the gasket.

14. The catheter introducer of claim 12 wherein the cap further includes a descending lip that defines an annular space for containing lubricant between the descending lip and the outwardly-facing surface of the gasket to lubricate medical instruments inserted through the gasket.

15. A catheter introducer comprising:

a housing having an inner bore, an outer bore proximal of and forming a juncture with the inner bore, and a shoulder defined at the juncture of the inner bore and the outer bore, the outer bore being larger in diameter than the inner bore;

a self-sealing gasket having a diameter corresponding substantially to that of the outer bore, including an inwardly facing surface contacting the shoulder and an outwardly facing surface;

an annular shelf formed distally of the shoulder and extending into the inner bore, the annular shelf defining a space in the inner bore that reduces the diameter of the inner bore, the annular shelf providing an annular abutment surface to limit deformation of the gasket when an instrument is inserted into the housing; and an end cap supported by the housing and contacting the outwardly facing surface of the gasket to secure the gasket in the housing.

16. The catheter introducer of claim 15 wherein the annular shelf has an inclined surface in and inward direction to allow limited deformation of the gasket in the inward direction.

17. The catheter introducer of claim 15 further comprising a circumferential ridge extending outwardly from the annular shoulder and contacting the inwardly-facing surface of the gasket to secure the gasket in the housing.

18. The catheter introducer of claim 17 further comprising a circumferential ridge extending inwardly from the end cap and contacting the outwardly-facing surface of the gasket to secure the gasket in the housing.

19. The catheter introducer of claim 15 whereby the gasket includes an annular ring extending from and beyond the inwardly facing surface of the gasket, and the shoulder of the housing defines an annular recess, the annular ring cooperating with the annular recess to secure the gasket in the housing.

20. A gasket for use in a catheter introducer comprising:

a self-sealing one piece gasket having an inwardly facing surface, an outwardly facing surface, and a central aperture in its outwardly facing surface, the aperture extending a predetermined depth into the gasket and terminating at a bottom wall;

an annular ring extending from at least one of the inwardly facing surface or the outwardly facing surface of the gasket;

a plurality of slits formed in the inwardly facing surface of the gasket and extending radially from a central region, the slits having a depth such that they intersect the bottom wall, the central region of the slits intersecting the bottom wall and defining a plurality of flaps normally closing the aperture;

the radius of the central aperture being substantially less than the radius defined by each of the slits to seal a range of diameters of devices that includes guidewires and catheters.

* * * * *